United States Patent
Johansen

(10) Patent No.: US 10,085,952 B2
(45) Date of Patent: Oct. 2, 2018

(54) DERMATITIS TREATMENT

(71) Applicant: Avexxin AS, Trondheim (NO)

(72) Inventor: Berit Johansen, Trondheim (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 14/647,765

(22) PCT Filed: Nov. 25, 2013

(86) PCT No.: PCT/EP2013/074612
§ 371 (c)(1),
(2) Date: May 27, 2015

(87) PCT Pub. No.: WO2014/082960
PCT Pub. Date: Jun. 5, 2014

(65) Prior Publication Data
US 2015/0290144 A1    Oct. 15, 2015

(30) Foreign Application Priority Data
Nov. 27, 2012  (GB) .................................. 1221329.4

(51) Int. Cl.
*A61K 31/121*    (2006.01)
(52) U.S. Cl.
CPC .................................. *A61K 31/121* (2013.01)
(58) Field of Classification Search
CPC ...... A61K 31/121; A61K 31/33; A61K 31/12; A01N 43/00; A01N 35/00
See application file for complete search history.

(56) References Cited

U.S. PATENT DOCUMENTS

2005/0165116 A1* 7/2005 Johansen ............. A61K 31/121 514/675
2010/0311843 A1* 12/2010 Johansen ............. A61K 31/121 514/666

FOREIGN PATENT DOCUMENTS

| JP | 8 109128 | 4/1996 |
|----|----------|--------|
| JP | 9143067 A | 6/1997 |
| JP | 2000 095683 | 4/2000 |
| JP | 2000508645 A | 7/2000 |
| JP | 2005518419 A | 6/2005 |
| JP | 2012-528813A A | 11/2012 |
| JP | 2012528813 A | 11/2012 |
| JP | 2013540713 A | 11/2013 |
| WO | 9738688 A1 | 10/1997 |
| WO | 03/063878 A1 | 8/2003 |
| WO | 2004-064715 A2 | 8/2004 |
| WO | 2007-075841 A1 | 7/2007 |
| WO | 2010-125340 A1 | 11/2010 |
| WO | 2010 139482 A1 | 12/2010 |
| WO | 2010139482 A1 | 12/2010 |
| WO | 2011 039365 A1 | 4/2011 |
| WO | 2011039365 A1 | 4/2011 |
| WO | 2012 02688 A2 | 1/2012 |
| WO | 201202688 A2 | 1/2012 |
| WO | 2012028688 A1 | 3/2012 |

OTHER PUBLICATIONS

Holmeide, et al., Journal of the Chemical Society, Perkin Transactions 1, , 2000, 2271-2276.
Ingber, et al., International Journal of Immunopathology and Pharmacology, Jan.-Mar. 2007; 20(1): 191-5.
Albanesi, et al., Current Opinion in Alergy and Clinical Immunology, 2010, 10:452-456.
Blauvelt, et al., J. Allergy Clin Immunol. vol. 111, No. 2, Feb. 2003.
English translation of Office Action issued in counterpart Japanese Patent Application No. 2015-543453, dated Jul. 13, 2017 (5 pages).
Anne Kristin Holmeide and Lars Skattebol, "Syntheses of some polyunsaturated trifluoromethyl ketones as potential phospholipase A2 inhibitors", Perkin 1, Jun. 30, 2000, 14, 2271-2276.

* cited by examiner

*Primary Examiner* — Sudhakar Katakam
(74) *Attorney, Agent, or Firm* — McCarter & English, LLP; Steven G. Davis

(57) ABSTRACT

A compound of formula (I)

R-L-CO—X    (I)

(wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;
L is a linking group forming a bridge of 1 to 5 atoms between the R group and the carbonyl CO wherein L comprises at least one heteroatom in the backbone of the linking group; and
X is an electron withdrawing group) or a salt thereof for use in the treatment of dermatitis.

15 Claims, 2 Drawing Sheets

DERMATITIS TREATMENT

This application is a National Phase application filed under 35 U.S.C. § 371 of PCT International Application No. PCT/EP2013/074612 with an International Filing Date of Nov. 25, 2013, which claims under 35 U.S.C. § 119(a) the benefit of Great Britain Application No. 1221329.4, filed Nov. 27, 2012, the entire contents of which are incorporated herein by reference.

This invention relates to the use of certain polyunsaturated long-chain ketones for the treatment of dermatitis and in particular to ketones carrying electron withdrawing substituents alpha to the carbonyl functionality in such treatment. The invention also relates to methods of treating dermatitis in patients comprising administration of the compounds of the invention to the patient, ideally topically.

BACKGROUND

In its broadest sense, dermatitis is inflammation of the skin. It is a common and disfiguring skin condition which requires quick and efficient treatment. Dermatitis symptoms vary, however, with the different forms of the condition. Symptoms vary from skin rashes to bumpy rashes through to flaky skin and blisters. Although different types of dermatitis have varying symptoms, there are certain signs that are common for all of them, including redness of the skin, swelling, itching, skin lesions and sometimes oozing and scarring.

Also, the area of the skin on which the symptoms appear tends to be different with every type of dermatitis. Types of dermatitis are classified according to the cause of the condition. Contact dermatitis is caused by an allergen or an irritating substance. Irritant contact dermatitis accounts for 80% of all cases of contact dermatitis.

Atopic dermatitis is very common worldwide and increasing in prevalence. Atopic dermatitis is a type of eczema and is an inflammatory, chronically relapsing, non-contagious and itchy skin disorder.

Other less common forms of dermatitis include dermatitis herpetiformis. It is characterized by intensely itchy, chronic papulovesicular eruptions, usually distributed symmetrically on extensor surfaces such as the back of neck, scalp, elbows, knees, back, hairline, groin or face.

Seborrheic dermatitis is a dermatitis that occurs in the vicinity of sebaceous glands and is caused by sebum over production. The condition tends to give a scaly, flaky skin condition.

Stasis dermatitis is an inflammation on the lower legs which is caused by build up of blood and fluid and it is more likely to occur in people with varicose veins.

Infective dermatitis is dermatitis secondary to a skin infection. A summary of dermatitis can be found in Blauvelt et al in Chapter 11 of J Allergy Immunol February 2003. Here the author, in particular, discusses allergic and immunological diseases of the skin, such as allergic contact dermatitis.

The present inventors seek new treatments for all types of dermatitis with particular emphasis on atopic dermatitis and contact dermatitis. The use of the compounds of the invention in allergic contact dermatitis is particularly considered.

There are numerous therapies for dermatitis on the market. Treatment of dermatitis is made according to the particular cause of the disease. Creams that contain corticosteroids are frequently used and simply avoiding the allergens and irritants are part of most treatment plans. For some types of dermatitis, non-steroidal medications may help relieve signs and symptoms. For all types of dermatitis, occasional use of over-the-counter antihistamines can reduce itching. Calamine lotion type products might be applied to the skin or a barrier cream such as zinc oxide or a suntan lotion might be used. For other conditions, a doctor might just advise letting the body's natural mechanisms sort the problem.

The present inventors have realised that the compounds discussed herein, compounds based upon long chain unsaturated fatty acid molecules, have potential in the treatment of dermatitis, in particular, atopic or contact dermatitis.

The compounds proposed for use in this invention have been disclosed before, for example, in EP-A-1469859 but only in the treatment of psoriasis which is a skin condition but is not a form of dermatitis. Psoriasis has very different biochemistry/immunology. The compounds have also been suggested, in WO2010/139482, for the treatment of glomerulonephritis or for the treatment of rheumatoid arthritis in WO2012/028688. The present inventors have realised that these compounds and others have utility also in the treatment of dermatitis.

It is generally accepted that the compounds of the present invention induce anti-inflammatory effects through modulation of TNFα initiated pro-inflammatory intracellular signalling cascades leading to transcription factor NF-κB activation in activated keratinocytes, which explains the compounds anti-inflammatory potential in diseases such as psoriasis and rheumatoid arthritis.

Oxazolone induced contact hypersensitivity in mice is a widely used model for delayed-type hypersensitivity (type IV hypersensitivity) with T-cell driven inflammation following challenge in previously sensitized skin. Examples of diseases where delayed-type hypersensitivity plays a significant role for disease development and clinical signs are Dermatitis including Contact Dermatitis and Atopic Dermatitis.

Psoriasis is an autoimmune induced, chronic disease of skin, characterized by T-cell accumulation, inflammation and hyperproliferation of keratinocytes in epidermis, as opposed to dermatitis being a delayed-type IV hypersensitivity disorder, the latter primarily driven by MHC class II restricted $CD4^+$ T cells.

The present inventors have surprisingly found that after oxazolone challenge, the compound of the invention surprisingly had marked anti-inflammatory effects shown by the ability to reduce oxazolone induced ear swelling. The effect was observed at very low concentrations of active compound (down to 0.01% active compound in the topical formulation) and shows that the compounds of the present invention surprisingly have anti-inflammatory effects through a previously unknown pathway that significantly inhibit delayed-type hypersensitivity mediated inflammatory pathways.

Consequently, the compounds of the present invention surprisingly have clinical beneficial effects in dermatitis including Contact Dermatitis and Atopic Dermatitis.

The present inventors have therefore shown that compounds claimed herein are able to suppress oxazolone induced delayed-type-hypersensitivity (DTH) responses in mice.

SUMMARY OF INVENTION

Thus, viewed from one aspect the invention provides a compound of formula (I)

$$R-L-CO-X \quad (I)$$

(wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group) or a salt thereof for use in the treatment of dermatitis.

Viewed from another aspect the invention provides a method of treating dermatitis comprising administering to an animal, preferably a mammal, in need thereof, e.g. human, an effective amount of a compound of formula (I):

R-L-CO—X      (I)

(wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group) or a salt thereof.

Viewed from another aspect the invention provides use of a compound of formula (I) or a salt thereof as hereinbefore described for use in the manufacture of a medicament for treating dermatitis.

DETAILED DESCRIPTION

This invention involves the use of compounds of formula (I) or a salt thereof in the treatment of dermatitis and related conditions.

Dermatitis

As noted above, the term dermatitis is broad and covers a variety of different skin conditions. Whilst it is envisaged that the compounds of the invention may have utility in treating a variety of different forms of dermatitis, it is preferred if the compounds are used to treat atopic dermatitis or contact dermatitis.

In particular, the compounds of the invention may be used to treat contact dermatitis such as allergic contact dermatitis or irritant contact dermatitis.

The nature of the allergan or irritant which causes the contact dermatitis can vary a lot and many people have different reactions to different allergans/irritants.

One of the most common causes of allergic contact dermatitis are plants of the *Toxicodendron* genus: poison ivy, poison oak, and poison sumac. Certain alkyl resorcinols such as bilobol found in *Gingko biloba* fruits are strong skin irritants. Other allergens include nickel, gold, balsam of Peru (*Myroxylon pereirae*), and chromium.

Common causes of irritant contact dermatitis are harsh (highly alkaline) soaps, detergents, and cleaning products. Irritant contact dermatitis can be divided into forms caused by chemical irritants and those caused by physical irritants. Common chemical irritants implicated include solvents (alcohol, xylene, turpentine, esters, acetone, ketones, and others); metalworking fluids (neat oils, water-based metalworking fluids with surfactants); latex; kerosene; ethylene oxide; surfactants in topical medications and cosmetics (sodium lauryl sulfate); alkalies (drain cleaners, strong soap with lye residues). Physical irritant contact dermatitis may most commonly be caused by low humidity from air conditioning. Also, many plants directly irritate the skin.

A further form of contact dermatitis is photocontact dermatitis. The skin condition is caused by exposure to ultraviolet light (320-400 nm UVA).

The invention requires the use of a compound of formula (I). The group R preferably comprises 5 to 9 double bonds, preferably 5 or 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 12 to 20 carbon atoms, especially 17 to 19 carbon atoms.

Whilst the R group can be interrupted by at least one heteroatom or group of heteroatoms, this is not preferred and the R group backbone preferably contains only carbon atoms.

The R group may carry up to three substituents, e.g. selected from halo, $C_{1-6}$ alkyl e.g. methyl, $C_{1-6}$ alkoxy. If present, the substituents are preferably non-polar, and small, e.g. a methyl group. It is preferred however, if the R group remains unsubstituted.

The R group is preferably linear. It preferably derives from a natural source such as a long chain fatty acid or ester. In particular, the R group may derive from AA, EHA or DHA.

The linking group L provides a bridging group of 1 to 5 backbone atoms, preferably 2 to 4 backbone atoms between the R group and the carbonyl. The atoms in the backbone of the linker may be carbon and/or be heteroatoms such as N, O, S, SO, $SO_2$. The atoms can form part of a ring and the backbone atoms of the linking group can be substituted with side chains, e.g. with groups such as $C_{1-6}$ alkyl, oxo, alkoxy, or halo.

Preferred components of the linking group are —$CH_2$—, —CH($C_{1-6}$alkyl)-, —N($C_{1-6}$alkyl)-, —NH—, —S—, —O—, —CH=CH—, —CO—, —SO—, —$SO_2$— which can be combined with each other in any (chemically meaningful) order to form the linking group. Thus, by using two methylene groups and an —S— group the linker —$SCH_2CH_2$— is formed. It will be appreciated that at least one component of the linker provides a heteroatom in the backbone.

The linking group L contains at least one heteroatom in the backbone. It is also preferred if the first backbone atom of the linking group attached to the R group is a heteroatom or group of heteroatoms.

It is highly preferred if the linking group L contains at least one —$CH_2$— link in the backbone. Ideally the atoms of the linking group adjacent the carbonyl are —$CH_2$—.

It is preferred that the group R or the group L (depending on the size of the L group) provides a heteroatom or group of heteroatoms positioned α, β, γ, or β to the carbonyl, preferably β or γ to the carbonyl. Preferably the heteroatom is O, N or S or a sulphur derivative such as SO.

Highly preferred linking groups therefore are —$NH_2CH_2$, —NH(Me)$CH_2$—, —$SCH_2$—, —$SOCH_2$—, or —$COCH_2$—

It is also within the invention for the linking group to be a ring or to comprise a ring. Thus for example, the linker might be thiophene, e.g. 2,4-thiophene which provides a two atom bridge to the carbonyl (via the shortest route). It would also be possible for the linker to comprise a ring such as furan, tetrahydrofuran, piperidine, cyclohexane, benzene or pyridine. Where the linker comprises a ring it is preferred if this is a 5 or 6 membered ring. It is preferred if the ring comprises at least one heteroatom or group of heteroatoms. It is preferred if the ring is unsaturated or aromatic. When the R and COX groups bind directly to such a ring, it is preferred if the R group and COX group bind on different atoms and preferred if they bind on carbon atoms of the ring.

The substitution pattern is preferably such that the R and carbonyl substituents are alpha, gamma to each other (i.e. 1,3 or 2, 4 or 3, 5-split).

For the avoidance of doubt, it is stressed that the 1 to 5 atom bridge should be counted as the shortest route from the start of the linker to the carbonyl.

Suitable ring linkers are shown below where the R group and carbonyl can bind to any two carbon atoms on these rings:

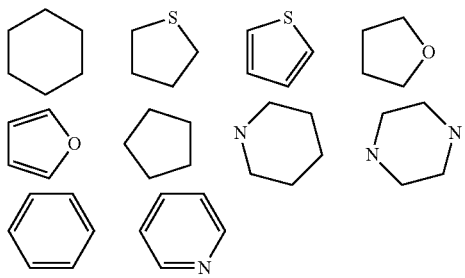

It is also within the scope of the invention for the linker to comprise a ring and non ring portion, e.g. $CH_2$-thiophene or $NH_2$-thiophene and so on. In such a linker it is preferred if the R group binds directly to the ring and that the carbonyl group binds to the non ring portion, e.g. a —$CH_2$— linkage. The skilled man will be able to devise all kinds of different linkers suitable for use in the invention.

Highly preferred linking groups are $SCH_2$, $NHCH_2$, $N(Me)CH_2$, 2,4-thiophene and 2,5-thiophene.

The group X is an electron withdrawing group. Suitable groups in this regard include O—$C_{1-6}$ alkyl, CN, $OCO_2$—$C_{1-6}$ alkyl, phenyl, $CHal_3$, $CHal_2H$, $CHalH_2$ wherein Hal represents a halogen, e. g. fluorine, chlorine, bromine or iodine, preferably fluorine.

In a preferred embodiment the electron withdrawing group is $CHal_3$, especially $CF_3$.

Thus, preferred compounds of formula (I) are those of formula (I')

R—Y1-Y2-CO—X wherein R and X are as hereinbefore defined;
Y1 is selected from O, S, NH, N($C_{1-6}$-alkyl), SO or $SO_2$ and
Y2 is $(CH_2)_n$ or $CH(C_{1-6}$ alkyl); or
Y1 and Y2 taken together form a 5 or 6 membered heterocyclic, optionally unsaturated or aromatic ring; or
Y1 forms a 5 or 6 membered heterocyclic, optionally unsaturated or aromatic ring and Y2 is $(CH_2)_n$;
where n is 1 to 3, preferably 1.

Highly preferred compounds for use in the invention are depicted below.

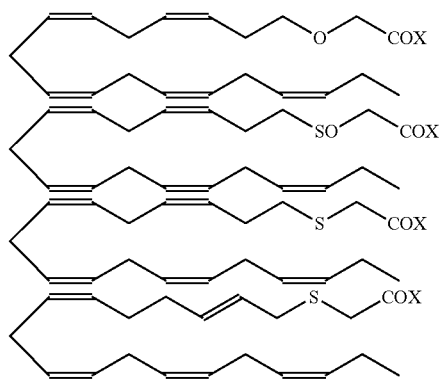

where X is as hereinbefore defined such as $CF_3$.

The following compounds are highly preferred for use in the invention:

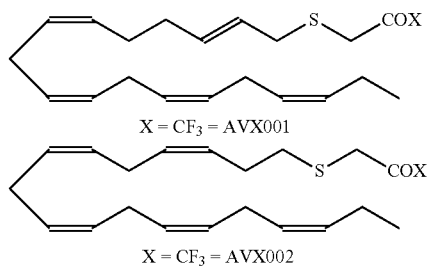

Where possible, the compounds of the invention can be administered in salt, solvate, prodrug or ester form, especially salt form. Preferably however, no such form is used.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

In a further highly preferred embodiment, the compound of the invention is a sulphonium salt. In such a compound, a sulphur atom in the backbone of the molecule, e.g. in the linker group, is functionalised to carry a C1-6-alkyl group. This can be achieved through reaction with an alkyl halide, e.g. methyl iodide. The halide ion forms the counterion of the salt.

In a further preferred embodiment therefore the invention provides a sulphonium salt of a compound of formula (I). Preferably the compound is of formula (VI)

where R and X are as hereinbefore defined and Z is a counterion, e.g. halide; e.g. the compound

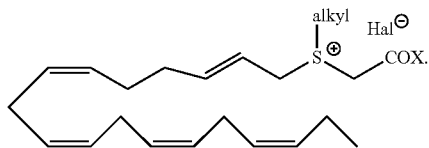

Compounds of formula (I) may be manufactured using known chemical synthetic routes. It is convenient to begin synthesis from the commercially available compounds arachidonic acid (AA), EPA (all-Z-eicosa-5,8,11,14,17-pentaenoic acid) or DHA (all-Z-docosa-4,7,10,13,16,19-hexaenoic acid). Conversion of the acid functionality of these compounds into, for example a —$COCF_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as $BrCH_2COCF_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

Where the backbone of the molecule contains a nitrogen atom, an alternative synthesis is required. Formation of a polyunsaturated alcohol can be achieved using protocols give in the above Perkin Trans paper. Thereafter, conversion of an alcohol —OH to —$NH_2$ with, for example, phthalimide and subsequent hydrazine reduction allows formation of a —$NH_2CH_2COCF_3$ group by reaction with trifluoropropyleneoxide (TFPO) and oxidation of the hydroxyl to a ketone. This reaction is shown below.

Methylation of the nitrogen can be effected before this reaction by the formation of an N-BOC group and reduction, e.g. with lithium aluminium hydride. Reaction with TFPO and oxidation yields the linker NMe-$CH_2$.

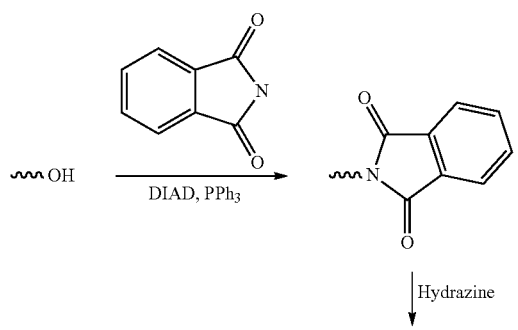

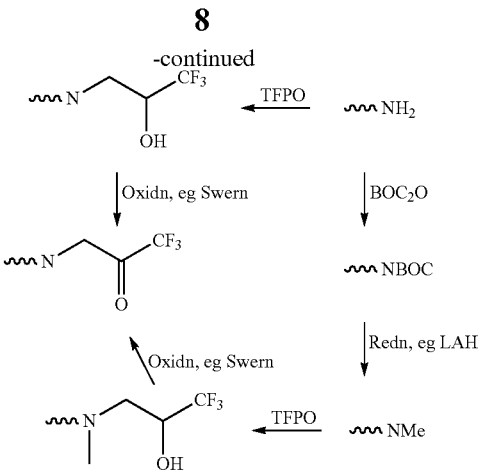

The compounds of the invention are proposed primarily for use in the treatment of, inter alia, dermatitis.

By treating or treatment is meant at least one of:
(i). preventing or delaying the appearance of clinical symptoms of the disease developing in a mammal;
(ii). inhibiting the disease i.e. arresting, reducing or delaying the development of the disease or a relapse thereof or at least one clinical or subclinical symptom thereof, or
(iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs. It is particularly preferred if the compounds of the invention are used therapeutically, i.e. to treat a condition which has manifested rather than prophylactically. It may be that the compounds of the invention are more effective when used therapeutically than prophylactically.

The compounds of the invention can be used on any animal subject, in particular a mammal and more particularly to a human or an animal serving as a model for a disease (e.g., mouse, monkey, etc.).

In order to treat a disease an effective amount of the active agent needs to be administered to a patient. A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the subject to be treated and will be ultimately at the discretion of the attendant doctor.

It may be that to treat dermatitis according to the invention that the compound of formula (I) has to be reapplied at certain intervals. Suitable dosage regimes can be prescribed by a physician.

While it is possible that, for use in the methods of the invention, a compound of formula I may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of dermatitis.

The active agent of the invention may therefore be combined with steroids or barrier materials (such as zinc oxide).

It will be appreciated that pharmaceutical compositions for use in accordance with the present invention may be in the form of oral, parenteral, transdermal, sublingual, topical, implant, nasal, or enterally administered (or other mucosally administered) suspensions, capsules or tablets, which may be formulated in conventional manner using one or more pharmaceutically acceptable carriers or excipients. The compositions of the invention could also be formulated as nanoparticle formulations.

However, for the treatment of dermatitis, the compositions of the invention will preferably be applied topically. They may be in the form of ointments, gels, syrups, creams and so on. Any conventional topical formulation vehicle may be used.

The pharmaceutical compositions of the invention may contain from 0.01 to 99% weight—per volume of the active material.

A therapeutically effective amount of the compound of the present invention can be determined by methods known in the art. The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

The compounds of the invention may be used to treat dermatitis in combination with other known pharmaceuticals for said purpose and this forms a further aspect of the invention. Other useful pharmaceuticals include corticosteroids and anti-histamines.

The invention is described further below with reference to the following non-limiting examples and figures.

EXAMPLES

Figure 1:
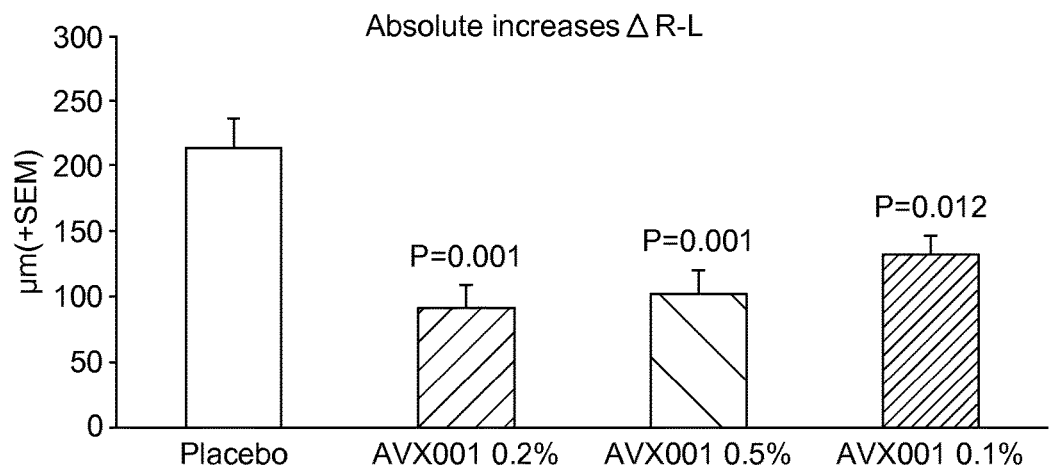
FIG. 1 shows the absolute increase in ear thickness of the right ear vs. the left ear for the oxazolone-induced ear edema model in mice at different therapeutic concentrations of AVX001.
Figure 2:
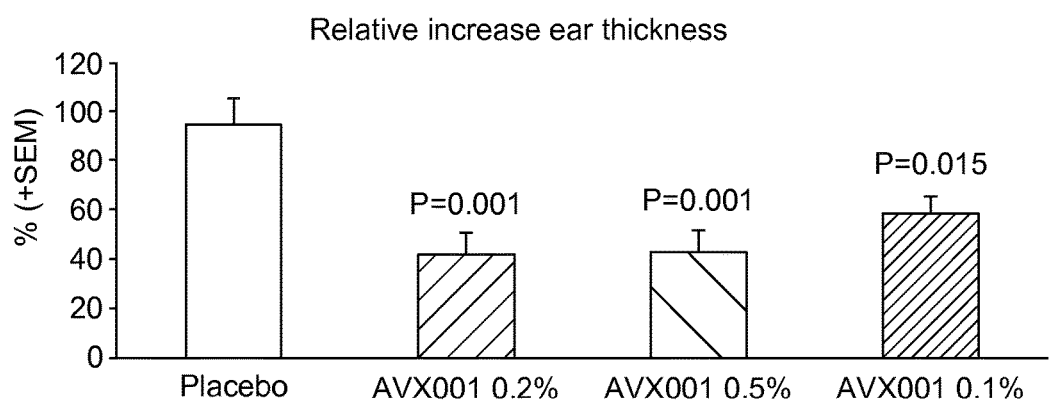
FIG. 2 shows the relative increase in ear thickness of the right ear vs the left ear for the oxazolone-induced ear edema model in mice at different therapeutic concentrations of AVX001.

The following compounds were used in the Experiments:

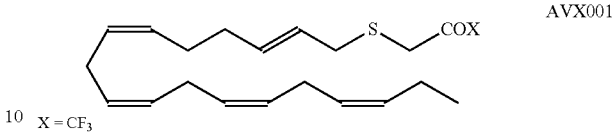

$X = CF_3$

Example 1—AVX001 in the Suppression of Oxazolone-Induced Delayed-Type-Hypersensitivity (DTH) Responses DTH can be induced by skin sensitization with oxazolone, followed by a topical ear challenge with oxazolone 7 days later. This challenge results in development of an inflammatory response in the ear within 24 hours, which is dependent on antigen-specific T cells. The DTH reaction is associated with the recruitment of a variety of inflammatory cells and development of edema. The latter can be measured by quantifying changes in ear thickness before and after ear challenge.

The oxazolone-induced ear edema model in mice is therefore a model of delayed contact hypersensitivity that permits the quantitative evaluation of the topical and systemic anti-inflammatory activity of a compound following topical administration.

EXPERIMENTAL

Female mice (6-8 wks—BALB/c) were acclimatization for 7 days in 12 hours light/12 hours dark cycle, at Temperature: 20-24° C., humidity: 55%±10%, on a standard laboratory mouse diet.

Delayed-Type-Hypersensitivity

Day 0: Mice were anesthetized by inhalation of 3-4% isoflurane in a 1:1 mixture of oxygen and medical air. The abdominal skin was shaved to enable topical application of 100 μl 1.5% (w/v) oxazolone in 100% acetone.

Day 7: All ears were wiped with ethanol to optimize exposure to oxazolone. Subsequently, the right ear of the sensitized animals were challenged by topical administration of 20 μl (10 μl on each side of the ear) 2.5% (w/v) oxazolone in 100% ethanol. The left ears were treated with 20 μl 100% ethanol.

Day 8: After 24 hours, mice were sacrificed and the right ears were collected to enable analysis by (immuno)-histochemistry and/or histology.

The vehicle used to carry AVX001 was paraffin. The placebo was paraffin. Approx 20 μl (10 μl on each side of the right ear) of composition is applied to effect the test.

Therapeutic Testing 4 groups (8 mice per group) were studied.

Group 1: Placebo, 1 hour and 7 hours after challenge

Group 2: Compound 0.2 wt %, 1 hour and 7 hours after challenge

Group 3: Compound 0.05 wt %, 1 hour and 7 hours after challenge

Group 4: Compound 0.01 wt %, 1 hour and 7 hours after challenge

Measurements:

Day 7: Ear thickness of both ears was measured directly before the ear-challenge (5 measurements per ear) using a Mitutoyo micrometer (accuracy 0.01 mm).

Day 8: 24 Hours after challenge, thickness of left and right ears was measured again.

The increase in ear thickness of each ear was calculated by subtracting the mean ear thickness measured on day 7 (before challenge) from the thickness on day 8 (24 hrs after challenge). To determine the oxazolone specific increase in ear thickness, the calculated increase in ear thickness of the left ear was subtracted from that of the right ear. Both absolute (Delta μm) and relative (%) increases in ear thickness were calculated.

Increase in Ear Thickness (Delta μm):

Thickness day 8 (μm)–Thickness day 7 (μm)

Oxazolone Specific Increase (Delta μm):

Increase right ear (Delta μm)–Increase left ear (Delta μm)

Relative Increase in Ear Thickness (%):

(Increase in ear thickness (Delta μm)/Thickness day 7 (μm))*100%

Relative Oxazolone Specific Increase in Ear Thickness (%):

Relative increase right ear (%)–Relative increase left ear (%)

Results:

In the placebo group a significant (p<0.0001) increase of 95% in ear thickness was observed, of the oxazolone challenged ear, compared with the ethanol challenged ear. The average thickness of the right ears increased from 230 μm on day 7 to 447 μm on day 8.

Effect of Treatment with AVX001

Treatment with AVX001 reduced the oxazolone specific ear swelling from 217 μm (placebo) to 134 μm (AVX001 0.01%), 103 μm (AVX001 0.05%) and 94 μm (AVX001 0.2%). The reduction of the oxazolone specific ear swelling caused by AVX001 was statistically significant for all concentrations.

Results are presented graphically in FIG. 1+2. Data is also presented in table 1 and 2.

Table 1/2

Summarizing Tables

TABLE 1

Absolute oxazolone specific ear swelling (Δ μm)

| Absolute Increase | Placebo | AVX001 0.01% | AVX001 0.05% | AVX001 0.2% |
|---|---|---|---|---|
| Average | 217 | 134 | 103 | 94 |
| SD | 64 | 43 | 54 | 50 |
| n | 8 | 8 | 8 | 8 |
| SEM | 23 | 15 | 19 | 18 |

TABLE 2

Relative oxazolone specific ear swelling %

| Absolute Increase | Placebo | AVX001 0.01% | AVX001 0.05% | AVX001 0.2% |
|---|---|---|---|---|
| Average | 95 | 58 | 43 | 42 |
| SD | 30 | 19 | 23 | 24 |
| N | 8 | 8 | 8 | 8 |
| SEM | 11 | 7 | 8 | 9 |

Example 2—Reduction in Ear Tissue PGE2 Enzyme after Treatment with AVX001

Figure 3:
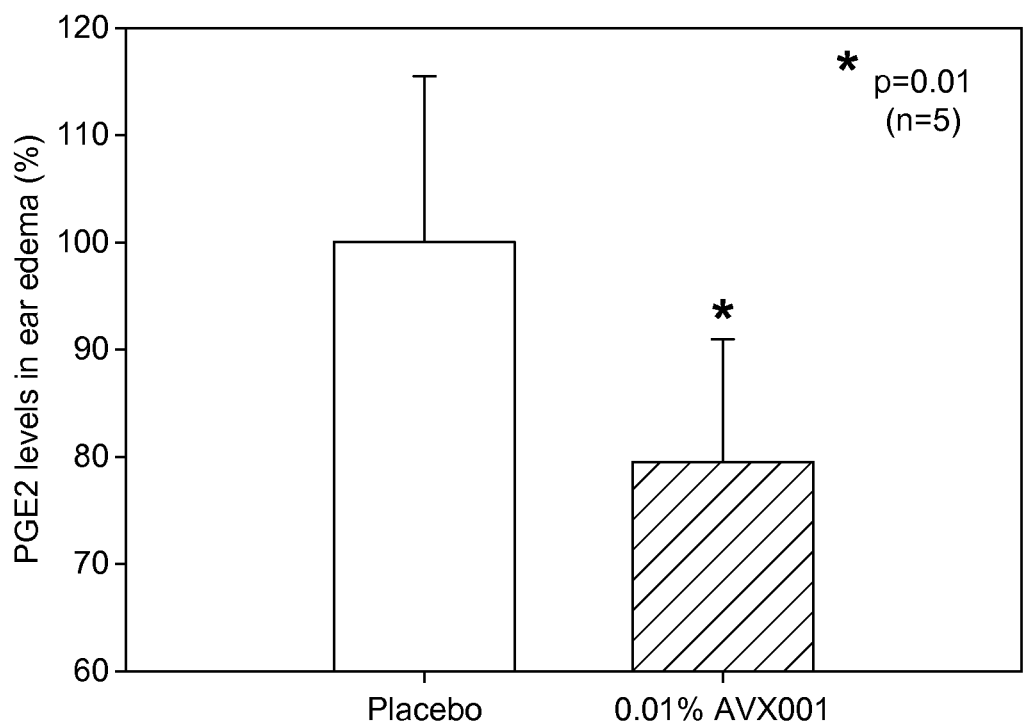
FIG. 3 shows the significant reduction (20%) in ear tissue PGE2 concentration in AVX-treated versus placebo ear tissue.

FIG. 3 shows the significant reduction (20%) in ear tissue PGE2 concentration in AVX-treated versus placebo ear tissue. PGE2 is a metabolite of arachidonic acid and the results show that the inhibitor AVX001 has hit its target, the group IVa PLA2 enzyme.

Materials and Methods (i) PGE2 EIA Analysis

Using a PreCellys homogenisator, the right ear biopsies were homogenized in 400 μl lysisbuffer containing 10 μM indomethasin. The lysate was stored at −80° C. until further processing. PGE2 EIA analysis ear homogenates was performed according to kit protocol (Cayman Chemicals). Plasma samples were diluted 1:60 and 1:180 in EIA buffer. The samples were hybridized over-night (18 hrs, 4° C.). The EIA plates were read using a Multiscan plate reader (Ascent Labsystems, OD550 nm). Ascent software for Multiscan, Version 2.4.1 was used to obtain the data. PGE2 results are shown as mean±SD relative to the paraffin-treated placebo mice (n=5 mice).

(ii) Statistical Analysis

Data of groups was examined by one-way analysis of variance, and individual groups were then compared with Dunnets test or Students t-test. Data was given as mean±SD, if not stated otherwise. Values of p<0.05 were considered significant.

The invention claimed is:

1. A method of treating atopic or contact dermatitis comprising administering to an animal in need thereof an effective amount of one or more of the following compounds:

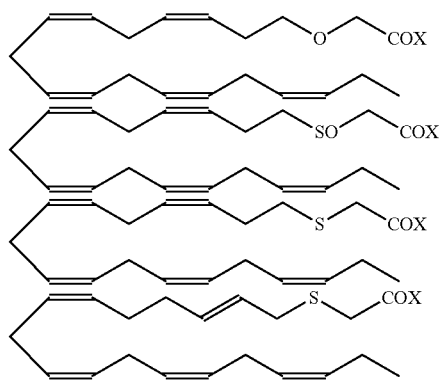

wherein X is an electron withdrawing group.

2. A method of claim 1 wherein X is $CF_3$.

3. A method of claim 1 wherein the animal is suffering from atopic dermatitis.

4. A method of claim 1 wherein the animal is suffering from contact dermatitis.

5. A method of claim 1 wherein the animal is suffering from allergen contact dermatitis.

6. A method of claim 1 wherein the compound is applied topically.

7. A method of claim 1 wherein the animal is a mammal.

8. A method of claim 1 wherein the animal is a human.

9. A method of treating atopic or contact dermatitis comprising administering to an animal in need thereof an effective amount of

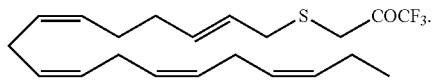

10. A method of claim 9 wherein the animal is suffering from atopic dermatitis.

11. A method of claim 9 wherein the animal is suffering from contact dermatitis.

12. A method of claim 9 wherein the animal is suffering from allergen contact dermatitis.

13. A method of claim 9 wherein the compound is applied topically.

14. A method of claim 9 wherein the animal is a mammal.

15. A method of claim 9 wherein the animal is a human.

* * * * *